(12) United States Patent
Hall et al.

(10) Patent No.: US 11,344,164 B2
(45) Date of Patent: May 31, 2022

(54) TOILET WITH SENSOR FOR DETECTING ANALYTICAL CONSUMABLE

(71) Applicant: Hall Labs, LLC, Provo, UT (US)

(72) Inventors: David R. Hall, Provo, UT (US); Scott Skousen, Lehi, UT (US); Scott R. Cleere, Provo, UT (US)

(73) Assignee: Medic, Inc., Provo, UT (US)

( * ) Notice: Subject to any disclaimer, the term of this patent is extended or adjusted under 35 U.S.C. 154(b) by 81 days.

(21) Appl. No.: 16/818,295

(22) Filed: Mar. 13, 2020

(65) Prior Publication Data

US 2020/0393475 A1    Dec. 17, 2020

Related U.S. Application Data

(60) Provisional application No. 62/912,429, filed on Oct. 8, 2019, provisional application No. 62/888,700, filed on Aug. 19, 2019, provisional application No. 62/888,972, filed on Aug. 19, 2019, provisional application No. 62/862,610, filed on Jun. 17, 2019.

(51) Int. Cl.
| | |
|---|---|
| *A61B 1/00* | (2006.01) |
| *A47K 5/12* | (2006.01) |
| *E03D 9/08* | (2006.01) |
| *A61B 10/00* | (2006.01) |
| *E03D 11/13* | (2006.01) |
| *G01N 1/28* | (2006.01) |
| *G01N 1/36* | (2006.01) |
| *G01N 21/78* | (2006.01) |
| *G01N 33/52* | (2006.01) |
| *G01N 35/00* | (2006.01) |
| *E03D 9/00* | (2006.01) |
| *E03D 9/03* | (2006.01) |
| *E03D 9/02* | (2006.01) |

(52) U.S. Cl.
CPC .......... *A47K 5/1217* (2013.01); *A61B 10/007* (2013.01); *A61B 10/0038* (2013.01); *E03D 9/005* (2013.01); *E03D 9/032* (2013.01); *E03D 9/08* (2013.01); *E03D 11/13* (2013.01); *G01N 1/28* (2013.01); *G01N 1/36* (2013.01); *G01N 21/78* (2013.01); *G01N 33/521* (2013.01); *G01N 35/00663* (2013.01); *E03D 2009/028* (2013.01); *G01N 2035/00673* (2013.01)

(58) Field of Classification Search
None
See application file for complete search history.

(56) References Cited

U.S. PATENT DOCUMENTS

2017/0322197 A1*  11/2017  Hall ............... G01N 33/493

* cited by examiner

*Primary Examiner* — Jyoti Nagpaul

(57) ABSTRACT

An analytical toilet is disclosed. The toilet includes a bowl for receiving excreta, a mechanism that uses a consumable for analyzing a sample of excreta, a storage structure for storing the consumable, a sensor that detects at least one property of the consumable, and a processor that generates an alert when the property is outside a predetermined parameter. The property the sensor detects can be used to determine at least one of the identity of the consumable, the quantity or supply of the consumable, or a property related to the suitability of the consumable.

20 Claims, 5 Drawing Sheets

TOILET WITH SENSOR FOR DETECTING ANALYTICAL CONSUMABLE

CROSS-REFERENCE TO RELATED APPLICATIONS

This application claims priority to U.S. Provisional Application Nos. 62/862,610 filed on Jun. 17, 2019, 62/888,700 filed on Aug. 19, 2019, 62/888,972 filed on Sep. 19, 2019, and 62/912,429 filed on Oct. 8, 2019. Each of the above are incorporated herein by reference in their entireties.

TECHNICAL FIELD

The present disclosure relates to smart analytical toilets. More particularly, it relates to analytical toilets with consumables, especially those associated with the health and wellness of the user.

BACKGROUND

The ability to track an individual's health and wellness is currently limited due to the lack of available data related to personal health. Many diagnostic tools are based on examination and testing of excreta, but the high cost of frequent doctor's visits and/or scans make these options available only on a very limited and infrequent basis. Thus, they are not widely available to people interested in tracking their own personal wellbeing.

Toilets present a fertile environment for locating a variety of useful sensors to detect, analyze, and track trends for multiple health conditions. Locating sensors in such a location allows for passive observation and tracking on a regular basis of daily visits without the necessity of visiting a medical clinic for collection of samples and data. Monitoring trends over time of health conditions supports continual wellness monitoring and maintenance rather than waiting for symptoms to appear and become severe enough to motivate a person to seek care. At that point, preventative care may be eliminated as an option leaving only more intrusive and potentially less effective curative treatments. An ounce of prevention is worth a pound of cure.

One form of health detection, analysis, and tracking is related to excreta. There are many types of consumables related to processing and analyzing excreta, such as reagents and additives. Additionally, there are consumables related to cleaning and sterilizing the testing environment, such as soaps, bleach, and abrasive media. Additionally, there are many consumables related to a person's health and wellness, including those that are part of treatments for a person, such as cleansers and soaps, lotions, ointments, medicaments, and other products that can be administered to a person.

A toilet with a reservoir tank of flush water is one example of a toilet that stores something for later use within the toilet (the use being to rinse the toilet bowl and flush the contents of the bowl into the sewer or septic system). These reservoirs are typically filled by a water supply pipe, such as one connecting to a municipal water supply. Generally, between the pipe and the reservoir is a mechanically operated valve where a float rises with the water level in the tank and the force of the water pushing up on the float actuates a mechanism that closes the valve. With time, a flush event, a leak, evaporation, and other phenomena can cause the water level to lower. As the water level in the tank lowers, the float falls and the valve opens. Occasionally, a toilet bowl cleaner tablet or another item containing cleaning additives is placed into the reservoir tank so cleaning additives dissolve or leach from the tablet into the water to additionally clean the bowl as part of a flush event. Such tablets and solid cleaning additives can work maintenance free for many flushes, often lasting weeks or months before needing to be replaced (the FAQ for the Clorox tablet claims it lasts 3 months with up to 10 flushes a day https://www.clorox.com/products/clorox-automatic-toilet-bowl-cleaner/unscented/).

Just a few examples of smart toilets and other bathroom devices can be seen in the following U.S. patents and Published Applications: U.S. Pat. No. 9,867,513, entitled "Medical Toilet With User Authentication"; U.S. Pat. No. 10,123,784, entitled "In Situ Specimen Collection Receptacle In A Toilet And Being In Communication With A Spectral Analyzer"; U.S. Pat. No. 10,273,674, entitled "Toilet Bowl For Separating Fecal Matter And Urine For Collection And Analysis"; US 2016/0000378, entitled "Human Health Property Monitoring System"; US 2018/0020984, entitled "Method Of Monitoring Health While Using A Toilet"; US 2018/0055488, entitled "Toilet Volatile Organic Compound Analysis System For Urine"; US 2018/0078191, entitled "Medical Toilet For Collecting And Analyzing Multiple Metrics"; US 2018/0140284, entitled "Medical Toilet With User Customized Health Metric Validation System"; US 2018/0165417, entitled "Bathroom Telemedicine Station." The disclosures of all these patents and applications are incorporated by reference in their entireties.

SUMMARY

In a first aspect, the disclosure provides an analytical toilet. The toilet includes a bowl for receiving excreta, a mechanism that uses a consumable for analyzing a sample of excreta, a storage structure for storing the consumable, a sensor for detecting a property of the consumable, and a processor that generates an alert when the property is outside a predetermined parameter. The property the sensor detects can be used to determine at least one of the identity of the consumable, the quantity or supply of the consumable, or a property related to the suitability of the consumable.

In a second aspect, the disclosure provides a method with the analytical toilet to detect the property of the consumable and send a signal with information about the property. Data from the signal is compared to a predetermined level and an alert is generated if the property is outside the predetermined parameter.

Further aspects and embodiments are provided in the foregoing drawings, detailed description and claims.

BRIEF DESCRIPTION OF THE DRAWINGS

The following drawings are provided to illustrate certain embodiments described herein. The drawings are merely illustrative and are not intended to limit the scope of claimed inventions and are not intended to show every potential feature or embodiment of the claimed inventions. The drawings are not necessarily drawn to scale; in some instances, certain elements of the drawing may be enlarged with respect to other elements of the drawing for purposes of illustration.

DETAILED DESCRIPTION

Figure 1:
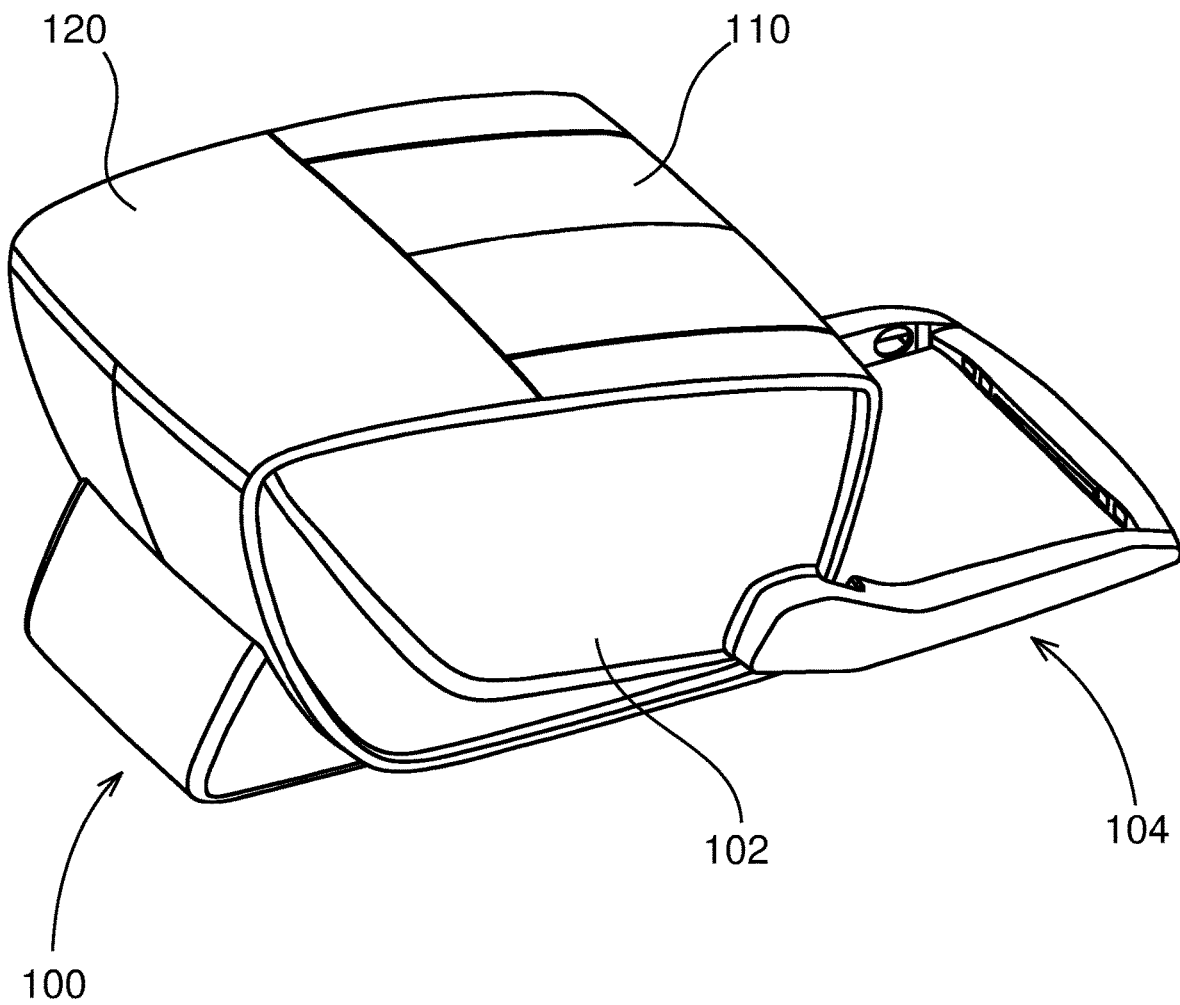
FIG. 1 is an isometric view of one embodiment of the invention.

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure and are not meant to be limiting in any fashion. Nor do these phrases indicate any kind of preference for the disclosed embodiment.

As used herein, the term "excreta" refers to any substance released from the body including urine, feces, menstrual discharge, and anything contained or excreted therewith.

As used herein, "toilet" is meant to refer to any device or system for receiving human excreta, including urinals.

As used herein, the term "bowl" refers to the portion of a toilet that is designed to receive excreta.

As used herein, the term "base" refers to the portion of the toilet below and around the bowl supporting it.

As used herein, the term "user" refers to any individual who interacts with the toilet and deposits excreta therein.

As used herein, the nouns "consumable", "consumable product", and similar terms are meant to refer to a product that is used by a process or in an application and must be resupplied in order for the process or application to happen again. Consumable is not meant to refer to untreated water in a toilet flush tank or pipe. In addition to the portion that is used by a process or in an application, the terms may also include a container structure for containing or holding the portion that is used by a process or in an application, such as a bottle, a cartridge, or other storage structure not part of the toilet's consumable storage structure. As used herein, the term "container" is meant to refer to a container structure as just described.

As used herein, the term "clean", "cleaning", and their variants are meant to refer to the absence or removal of foreign or extraneous matter, especially excreta, residual chemicals, dust, and other material. For example, feces or other material from a previous user could interfere with health and wellness analysis in a toilet, therefore any test equipment would need to be clean of those things prior to receiving a new sample. As another example, biological material from a user could spread disease to a subsequent user, therefore toilet components that could spread contaminates to user would need to be cleaned between toilet uses.

As used herein, the terms "sanitary", "sanitize", "sanitization", and their variants are meant to refer to the absence or destruction of microorganisms and fall under the broader umbrella of "clean" and variations thereof.

As used herein, the term "sensor" is meant to refer to any device for detecting and/or measuring a property of an organism or substance regardless of how that property is detected or measured, including the absence of a target molecule or characteristic.

As used herein, the term "controller" is meant to refer to the component of a device that contains the circuitry necessary to interpret and execute instructions fed into the device. A controller may also be called a "control unit" and "processor."

As used herein, the term "alert" when originating from a "processor" is meant to refer to a signal from the processor indicating a specific state, event, or condition. Often, action may be undertaken as a response to the state, event, or condition which the alert represents.

As used herein and when used in relation to electronic data, the term "operation" is meant to refer to an action resulting from a single instruction and includes temporarily storing the data, writing the data to a long term memory location, transmitting the data, comparing the data to other data, or initiating another operation.

As used herein, and particularly when related to the use of a consumable, the term "analysis" and its variants are meant to refer to an analysis event assessing a user's health and wellness, and/or any pre- or post-processing performed as a result of or in conjunction with the analysis event.

As used herein and when related to analysis of excreta, the term "integrity" and other similar terms are meant to refer to the reliability of results from an analysis.

As used herein, especially when referring to a consumable, the term "new supply" is meant to cover making the current supply usable or replacing the supply. This includes adding more consumable product to what is already there, removing the consumable product and replacing it with other consumable product, or modifying the existing consumable product that is already there. Modifying the existing supply may include removing some of the supply or changing the state of the supply, such as temperature, pressure, humidity, or exposure to light.

As used herein, the term "criterion" is meant to refer to the standard or test by which something is judged, such as a predetermined preference regarding a property or state of a consumable product. In general, the result of testing something against a criterion is determining whether the said something meets or does not meet the standard.

As used herein, the term "environmental condition" is meant to refer to one or more property of the environment the consumable is in which affect one or more the property of the consumable, such as temperature, pressure, humidity, light, and other electromagnetic radiation.

As used herein, the term "maintenance" is meant to refer to any upkeep required to keep something functioning as intended. With regard to stored consumables in a toilet, maintenance may include making sure that the correct consumable is there, the consumable has not expired or perished, there is enough consumable available, and that preferred environmental conditions are maintained in order to extend or optimize the life of the consumable.

As used herein, the terms "maintenance request" and "maintenance alert" are meant to refer to an indication that maintenance may be required.

As used herein when referring to a consumable, the terms "suitable", "suitability", and other variants are meant to refer to when the consumable is acceptable for use. For example, a nonpreferred consumable may be unacceptable for use. Additionally, a consumable that is acceptable for use may become unacceptable for use. For example, some consumables may degrade or loose potency with time. Additionally, a consumable exposed to non-ideal temperatures, pressures, humidity, or electromagnetic radiation may experience negative affects regarding its degradation rate or potency.

Exemplary Embodiments

The present disclosure relates to the detecting and monitoring of consumables, products, or similar descriptors within a toilet, especially those related to cleaning and sterilizing the toilet, those which might be administered to a user for their health and wellness, and those used in sampling, processing, or analyzing of excreta within the toilet. More specifically, this disclosure relates to using a sensor to detect and monitor the presence, identity, amount, and/or other property of a consumable and a processor generating an alert based on the property. These alerts may comprise a number of things, including automatic decision making within the toilet regarding the toilet's functions (especially those which use or are related to one or more consumable), providing this information to an external electronic system, generating a maintenance alert for the toilet, and/or automatically requisitioning a new supply of the consumable. To enable the generation of an alert, there may be a predetermined preference and/or criterion against which the property of the consumable may be compared or an input to.

One benefit of the present invention is providing automated assistance in making sure desired consumables are and/or will be available for future use within a toilet. There are many different criteria that may be important in providing this benefit and many properties that may be relevant to determining whether a criterion has been met. This can include automatic monitoring of one or more consumable to: identify what consumables are available for use within the toilet, determine the quantity of a consumable remaining, estimate the number of uses still available for a consumable, estimate the time period the consumable will remain available for use, estimate whether or not the consumable is still useable, monitor the temperature of the consumable, measure the pressure of the consumable, measure the moisture content of the consumable, provide information about the consumable to an external receiver or recipient, generate data regarding the use or storage of the consumable, receive date regarding the use or storage of a consumable, compare any data about the consumable to other data regarding its use or storage, and automatically reorder or restock a consumable. Specifically, a sensor can detect a consumable or product, determine if the consumable or product is being preserved properly or if it will need to be replaced soon, and then necessary maintenance can be performed to ensure the consumable will be available when needed.

Another benefit is being able to automatically select whether one or more toilet features or functions are available based on whether or not a desired consumable is available and ready for use by the toilet.

Figure 2:
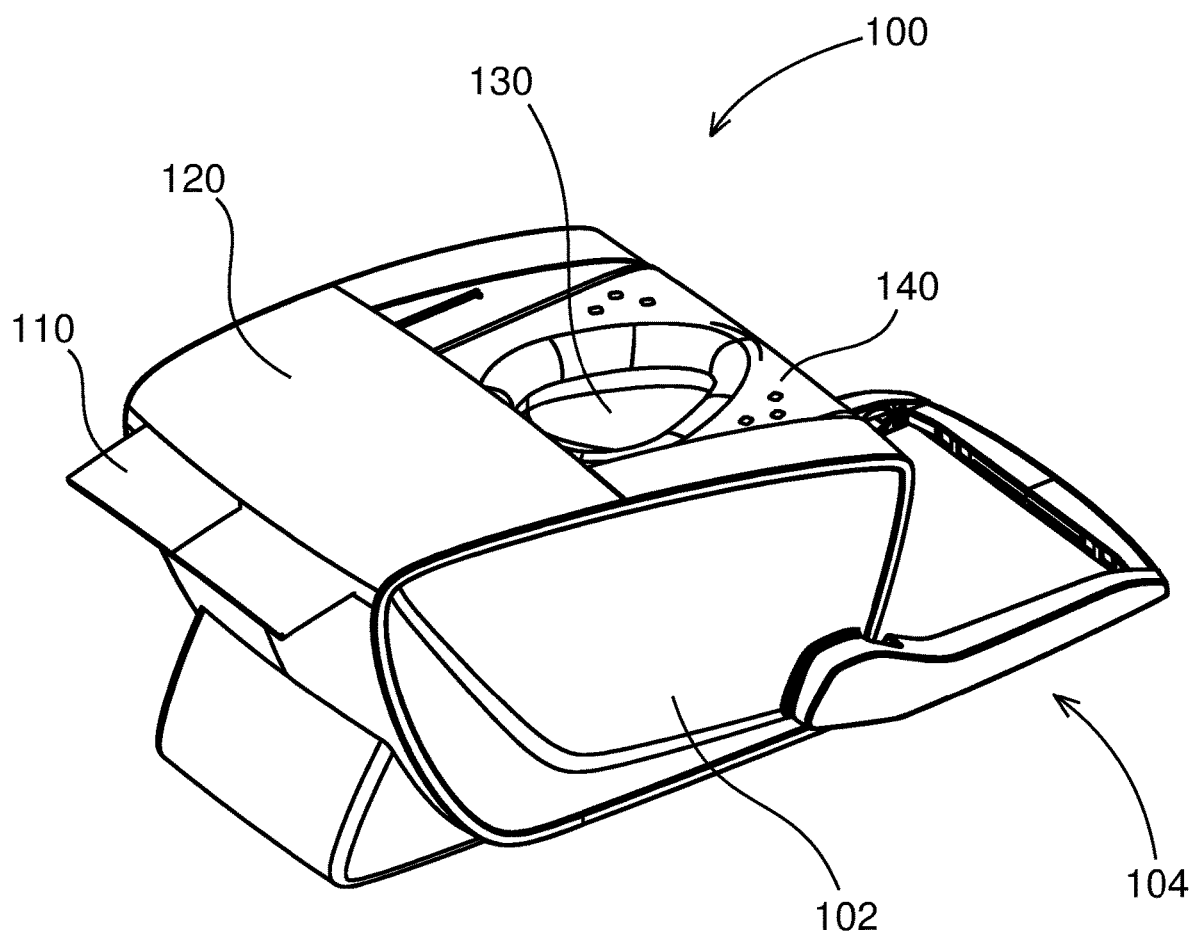
FIG. 2 is an isometric view of one embodiment of the invention.
Figure 3:
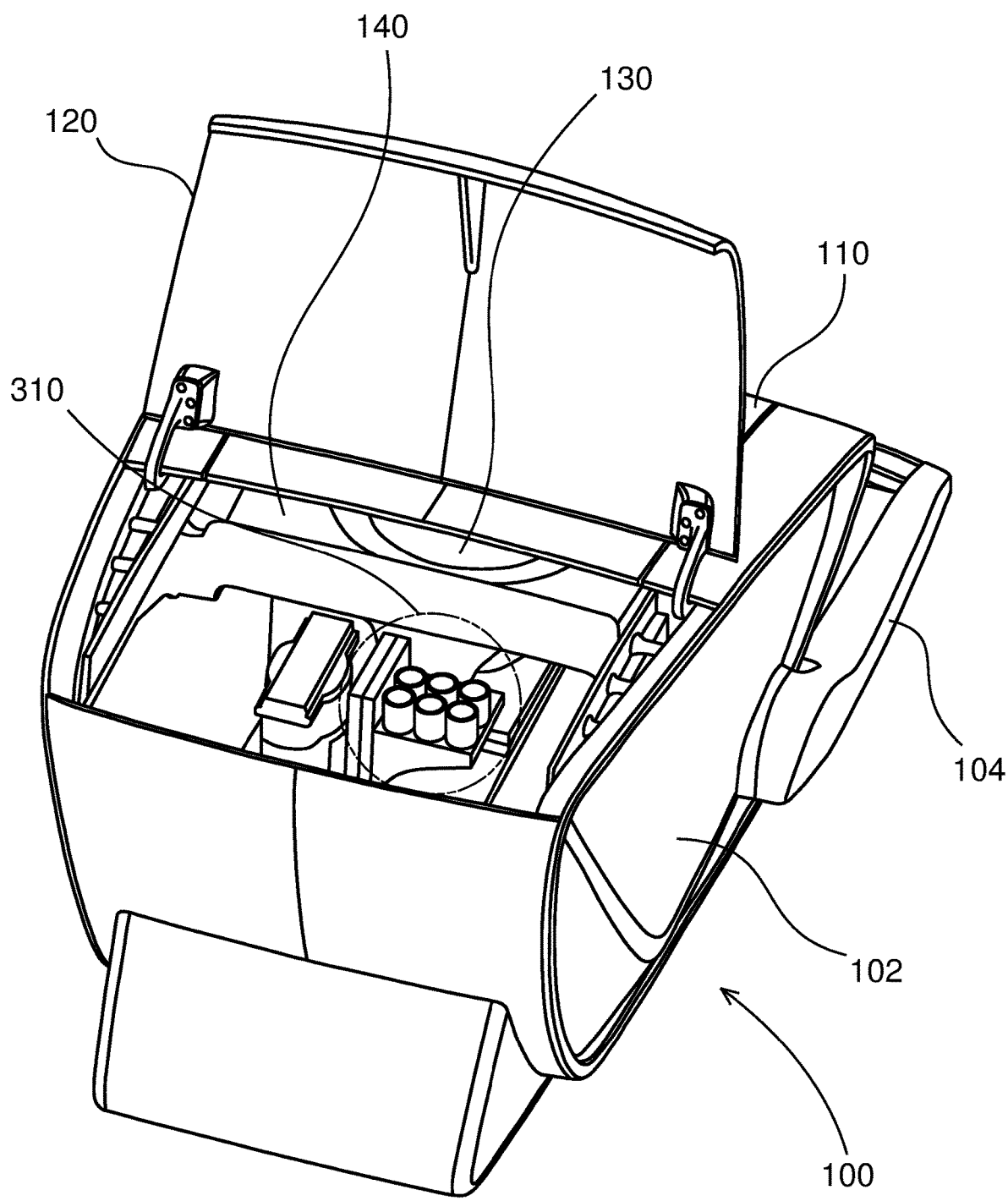
FIG. 3 is a detail view of one embodiment of the invention.

Now referring to FIGS. 1-3, a preferred embodiment of toilet 100 is shown. Toilet 100 includes exterior shell 102, equipment cover 120, bowl 130, seat 140, lid 110, and foot platform 104. Housed within toilet 100 are a variety of features, including equipment, that facilitate receiving excreta, processing excreta for analysis, analyzing excreta, and disposing of excreta. FIG. 1 shows toilet 100 with lid 110 closed. This prevents a user from sitting on seat 140 and depositing excreta in toilet 100 until the toilet is ready for use. FIG. 2 shows toilet 100 with lid 110 open so a user can stand on platform 104 or sit on seat 140 and deposit excreta in toilet 100. FIG. 3 shows toilet 100 with lid 110 closed and equipment cover 120 open allowing access to equipment housed within toilet 100. With exterior cover 120 open, consumable storage 310 inside the toilet is accessible.

Consumable storage does not have to be limited to one location within the toilet. In an alternative embodiment, the storage of consumables occurs in multiple locations throughout the interior of the toilet. Alternatively, at least one consumable is stored outside of the toilet. The consumables stored outside of the toilet may be for use with components comprising the toilet (including in the bowl area) or it may be for a piece of equipment used in conjunction with the toilet such as exterior analysis equipment connected to the toilet or a bidet separate from the toilet which a user would use to wash themselves after using the toilet.

Figure 4:
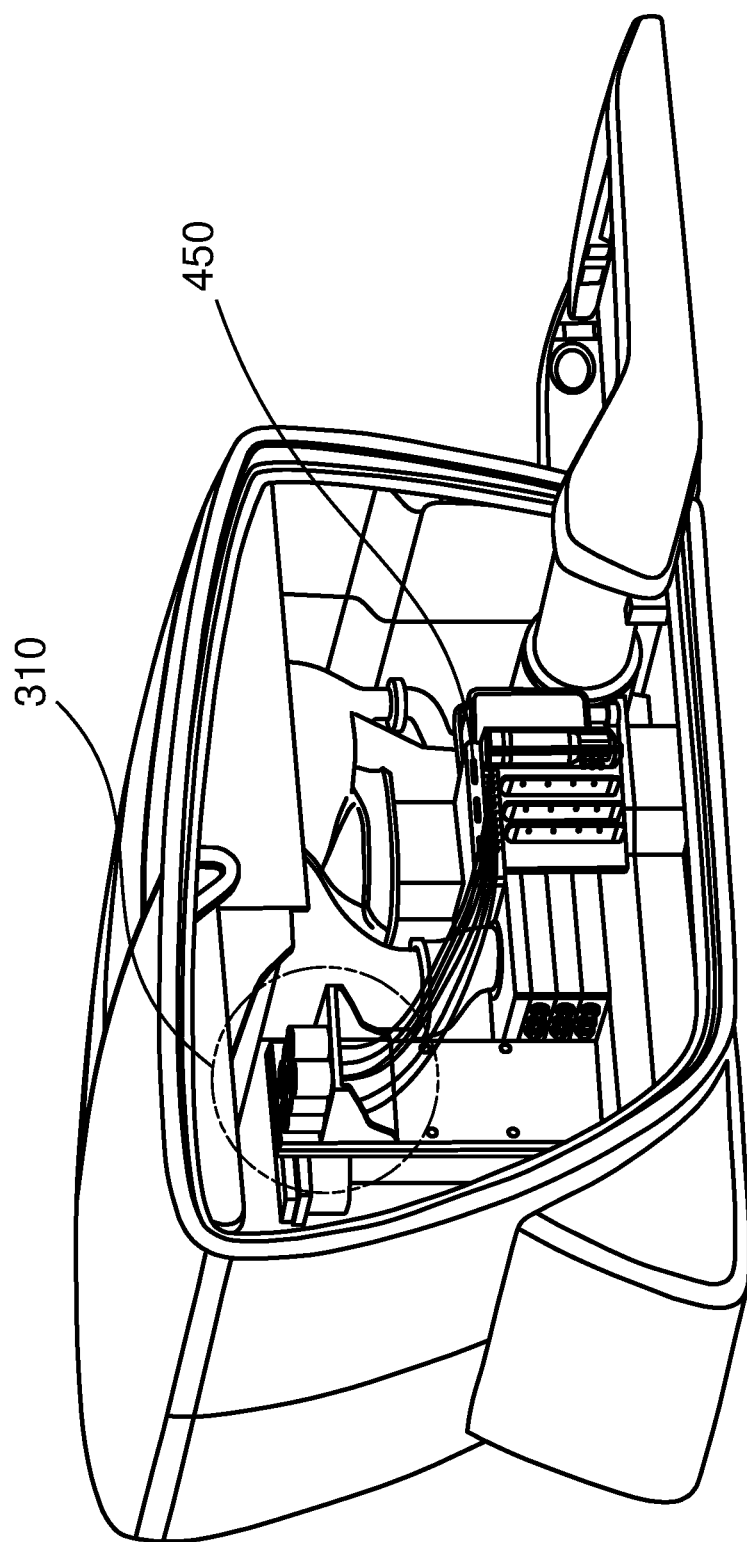
FIG. 4 is a detail view of one embodiment of the invention.
Figure 5:
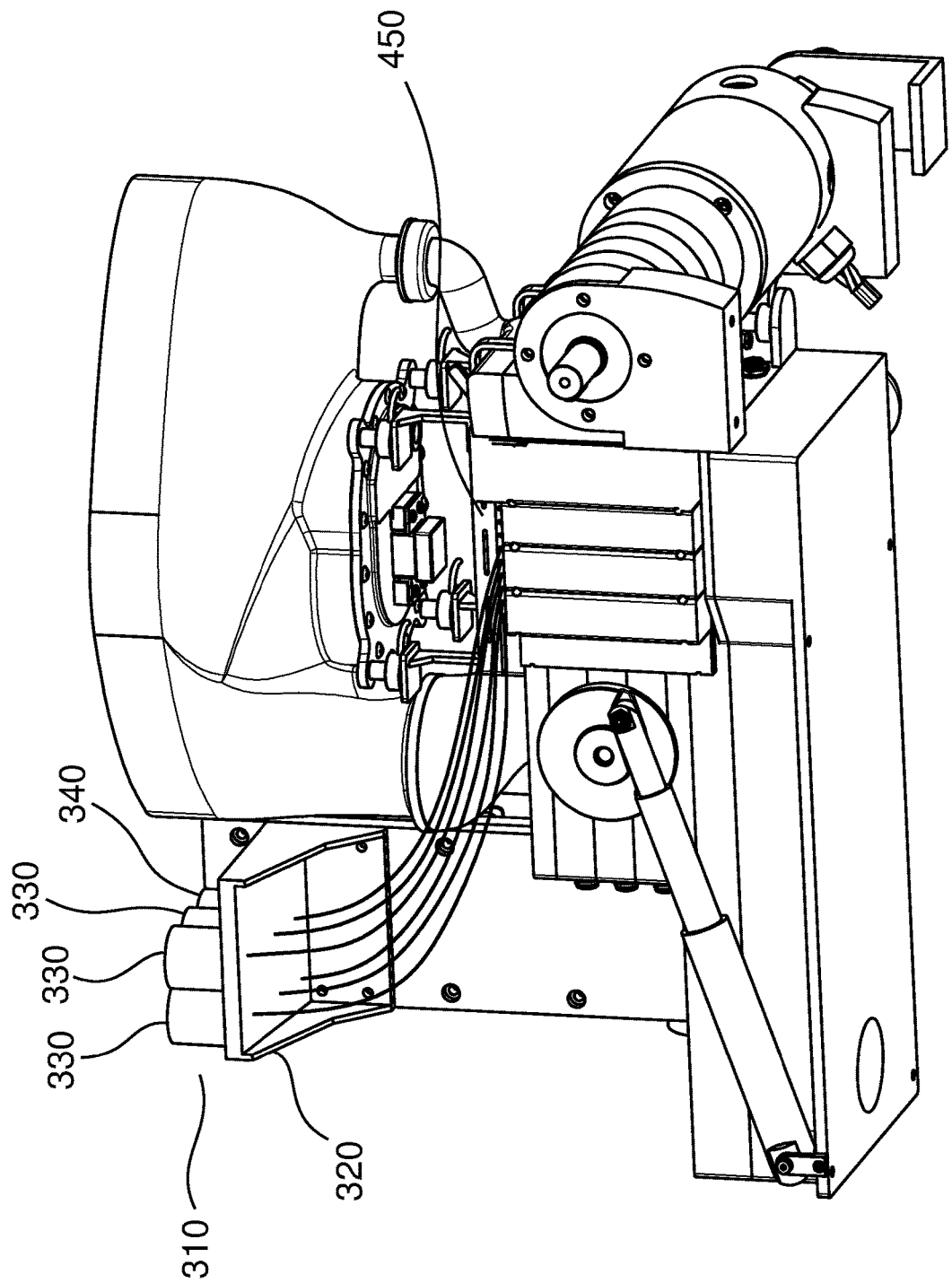
FIG. 5 is a detail view of one embodiment of the invention.

FIGS. 4 and 5 show interior portions of toilet 100. Exterior shell 102 and other components are not shown so as to facilitate viewing of features, including equipment, housed within toilet 100.

In one preferred embodiment, toilet 100 is configured so the consumables are received by storage structure 320 in storage area 310. Storage structure 320 may have one or more storage compartment 330 which help hold a consumable while it is in storage area 310. Some consumables include their own storage structure in conjunction with the portion of the consumable that is used by the toilet. In one preferred embodiment, the toilet storage structure has cavities or matting portions configured to receive or connect with the container the consumable products come in from the supplier. In another preferred embodiment, the storage structure has a specific container it is designed to receive, and the consumable product is loaded into a container of that type in conjunction with being stored in the storage area. In an alternative preferred embodiment, the storage structure is designed to receive and store the consumable separate from the container in which it was shipped or sold.

There are many desirable configurations and material choices for the storage structure. The selection of these choices depends on many factors, including how consumables are packaged when they arrive from a supplier, the corrosive or other potentially harmful characteristics of the consumable, environmental storage requirements of the consumable such as temperature, the facilitation of using a sensor to detect a property of the consumable (e.g., transparent containers allowing monitoring with light and/or cameras), the maximum number of consumables to be simultaneously stored, the volume or quantity of various consumable to be stored, the weight of consumable to be stored, toilet design decisions that affect how the storage structure can be mounted in the toilet, and toilet design decisions that affect the size of the storage area. In one preferred embodiment, the storage structure is plastic with a generally flat shelf, one or more cylindrical extrusions going up from the shelf that each receive a container, and a sealed material pathway for each container leading from the consumable in the container and to a connection point, which connection point facilitates connecting to a manifold, solenoid, or other means of controlling the flow and selectively distributing the consumable within the toilet. In alternative embodiments, the storage structure may be made from metal, ceramic, rubber, glass, and stone. Alternatively, the storage structure is a combination of different materials.

There are many desirable configurations and material choices for a container, if one is used. Similar to the storage structure, the selection of these choices depends on many factors, including how consumables are packaged when they arrive from a supplier, the corrosive or other potentially harmful characteristics of the consumable, environmental storage requirements of the consumable such as temperature, the facilitation of using a sensor to detect a property of the consumable, the volume or quantity and weight of the consumable to be stored. Any type of container material may be suitable if the material properties meet the functional needs of the container. Preferred materials include plastic, metal, ceramic, rubber, plastic, stone, and wood. Some preferable container types are a bottle, a reel, a bag, a box, and a can. More preferably, the container is a clear or translucent plastic bottle. In one preferred embodiment, the container includes an RFID tag, QR code, bar code, or other mechanism which identifies the consumable. Many varieties of container types, sizes, and materials are acceptable so long as the combination meets the functional needs of the toilet.

Preferably, toilet 100 has a connection from each consumable in consumable storage 320 to manifold 450 which allow transportation of at least a portion of each consumable to manifold 450. From manifold 450, the consumable can be selectively directed to wherever in toilet 100 the consumable is needed for a desired use. For example, an ointment may be loaded into the toilet as a consumable and a user of the toilet may desire the toilet applies the ointment to the user while the user is seated on the toilet. Upon receiving the instructions to do so, the toilet could direct the ointment into a bidet or other applicator which applies the ointment to the user. In a second example, the toilet may test for the presence of various compounds in feces. A portion of feces deposited into the toilet may be mixed with water and directed into one or more testing location in the toilet. The manifold may direct one or more reagent to each analysis location to facilitate testing for the various compounds. In a third example, a cleaning additive may be a consumable loaded into the storage structure. After excreta is no longer needed, the manifold may direct a portion of the cleaning additive into a stream of water applied to parts of the toilet that contacted excreta.

There are many different kinds of consumable that may be preferred for use within or by the toilet. A consumable product may be used individually by the toilet or in combination with others. Similarly, a toilet that uses one kind or class of consumable may also use another kind or class. Explained below are various class or classifications of consumable, some uses thereof, and some mechanisms that use a consumable.

One general class of consumable is those useful for cleaning and/or sterilizing the toilet, especially those components of the toilet which come in contact with excreta. Examples include treated tap water, distilled water, deionized water, a cleaning additive, a sterilizing additive, and a soap. Other common consumables in this category include detergents, ammonia solutions, bleach, citric acid, lye, vinegar, various forms of alcohol, borax, backing soda, acetone, and nitrates. As an example, tap water is often used to flush excreta from a toilet—in residential applications, the supply pipe feeds into a flush tank in preparation for flushing. In a toilet that receives and analyzes excreta, it is important before each test cycle to remove any foreign or extraneous contaminant matter that may interfere with sample processing or analysis, whether those contaminants are from excreta, leftover consumables, or other sources. To help with the removal of excreta from toilet surfaces, an abrasive media such as a powdered calcite, feldspar, quartz, or silica may be added to the water before it is flushed through the toilet. Additionally, a disinfectant such as bleach may be added to kill any pathogens in the toilet or on surfaces that contact a user, such as a toilet seat, a lid, a backrest, or an armrest.

In one embodiment, the toilet contains fluidic pathways to carry samples to and away from preparation and analysis portions of the toilet. In addition to these pathways and areas being exposed to excreta, additional chemicals, like reagents, may be used on the sample to prepare the sample for testing, test the sample, or postprocess the sample (like prepare the sample for disposal). These portions of the toilet will not necessarily be used for the same test or have the same reagent each time, meaning different chemicals may be used over time in the same area. It's possible that residue from a chemical related to a previous analysis could adversely react with a chemical related to a future analysis, including compromising the testing, destroying components of the toilet, or even being a hazard to nearby or downstream life and objects. Thus, it is important to clean areas of the toilet that receive, process, analyze, and dispose of excreta and chemicals.

In one preferred embodiment, the toilet is self-cleaning and includes a mechanism for cleaning a portion of the toilet. More preferably, a consumable that facilitates cleaning is incorporated with the self-cleaning functionality of the toilet. For example, the cleaning mechanism may be flushing portions of the toilet with water and any of a variety of cleaning consumables may be added to the water to improve final cleanliness of the toilet. In one preferred embodiment, the water is gravity fed through from a flush tank of stored water. In another embodiment, the flush water comes from a pressurized water pipe supplying water to a building the toilet is in. In another example, the toilet includes a water pump to pressurize the water. In one embodiment, the mechanism includes a bidet-like or nozzled device that can direct a stream or jet or water to clean areas of the toilet. In one preferred embodiment, the mechanism includes a squeegee or similar device that mechanically pushes or scrapes contaminants from surfaces of the toilet. Another embodiment of the mechanism applies or distributes emulsifiers or similar consumables that break down contaminates. Similarly, another embodiment of the mechanism applies a chemical that neutralizes foreign or extraneous matter. In another preferred embodiment, the mechanism is used electromagnetic radiation, such as UV or microwave portions of the electromagnetic spectrum, to clean portions of the toilet, flush water, or another consumable. Alternatively, the mechanism includes a heat source applied to portions of the toilet, flush water, or another consumable. Portions of the toilet that may be cleaned include the bowl, excreta processing areas, excreta analyzing areas, surfaces a user comes in contact with (like the seat, lid, arm rests, and user operated controls), or ancillary portions of the toilet that do not directly contact any of the above portions of the toilet but whose contamination could contaminate the above because they are still in material communication with them.

In another embodiment, the toilet extends above the toilet seat and includes features that might serve as a back rest or an arm rest. These include surfaces which may have contact with a user and may need to be cleaned between users or uses by the same user. Additionally, these or other features may provide the toilet with access to the trunk portion of a user's body. Access to the trunk can facilitate analysis of the user and/or administering a product to a user. For example, the toilet may have sensors that contact a user's back which are attached to the toilet lid. As another example, a toilet may have an armrest to one side of the toilet seat which a user can use to support his or her weight. The structure supporting the armrest can be used to support a sensor, an automated hypodermic needle, or another device capable of analyzing a user, administering a product to a user, or cleaning and/or sterilizing the toilet. Regardless of the device, any portions that contact a user or enable something else to contact a user may benefit from being automatically cleaned by a consumable in stored in the toilet. For example, a bidet-like device that administers a deodorizing gas or a medicated cream to a user may not directly contact a user, but it enables something from the toilet to contact the user. If the material pathway in the bidet-like device were to become contaminated, the product could likewise become contaminated and could have a negative interaction with the user.

Another general class of consumables is those products which are administered to a person to improve the person's health and wellness. One way to categorize such products is to split them into medicaments—which are prescribed by a health care professional—and those that are not medicaments. Whether prescribed or not, these products can be administered to a user of the toilet in many ways, including topically or transdermally (applied to skin), parenterally or subdermally (below the skin), enterally or transmucosally (into the gastrointestinal track or onto mucus membranes), or through inhalation (through the respiratory system). Each method lends itself to various delivery methods which affect the both the consumable itself and mechanisms of the toilet.

For example, topical consumables may come in the form of a soap, a disinfectant, a solution, a moisturizer, a lotion, an ointment, or a cream. They are generally intended to affect the area of the body in the area where they are applied. These items may be applied directly to a person's epidermis or they may be mixed with something else. Examples include a soap being mixed with water being sprayed on a user through a bidet, a medicament being mixed with an ointment which is mechanically applied to user by a robotic applicator arm, and a moisturizing cream may seep through the toilet seat to the user.

Transdermal administrations are generally less focused on affecting the area of the body where they are applied and are more focused on affecting parts or systems of the body away from the location they are applied. They are often applied for longer periods of time and a common way to achieve this is to use an adhesive patch, ointment, or gel that keeps the product in contact with the skin. In one preferred embodiment, the toilet applies an adhesive patch to a user and the patch stays on the user for a period of time after they leave the toilet. Additionally, the toilet may also automatically remove an adhesive patch. Alternatively, the toilet may directly apply a transdermal product to the skin, which may or may not remain on the user after the user leaves the toilet. Transdermal administration may be accompanied by the creation of microchannels, which are created by use of a micro-needling device. As of December 2018, there were 54 transdermal patch products being marketed in the United States (https://www.ncbi.nlm.nih.gov/pmc/articles/PMC6321070/).

For example, the first transdermal patch approved by the FDA was Transderm Scop®, which can deliver scopolamine to prevent nausea and vomiting from motion sickness for up to 3 days. Additional products deliver nicotine, fentanyl (opioid), nitroglycerine (antianginal), buprenorphine (opioid), ensam (antidepressant), daytrana (transdermal Ritalin), scopolamine (anti-nausea), estrogen and testosterone, contraceptive medication, clonidine (blood pressure medication), and rivastigmine (Alzheimer's treatment).

Parenteral or subdermal products are administered—usually by needle—through the skin. Typical injection depths include intramuscular, subcutaneous, intravenous, and intradermal. Each of these depths can be achieved through various methods. Common methods include the needle entering the skin from approximate angles for each depth as follows: intramuscular @ 90° or perpendicular to the skin, subcutaneous @ 45°, intravenous @ 25°, and intradermal @ 10°-15°. Most parenteral or subdermal products take the form of solutions, but there are some such as an implant that releases product to the body over time. Some common parenteral and subdermal products include insulin, vaccines, contraceptives, human chorionic gonadotropin, testosterone, b12, heparin, and allergy medicaments.

In one preferred embodiment, the toilet includes a hypodermic needle through which a product can be injected into a user. More preferably, the angle and depth of needle insertion into the user are automatically controlled. In one preferred embodiment, the toilet applies a topical cleaner or sterilizer to the injection side prior to administering the injection. In one preferred embodiment, the toilet may take a blood sample prior to administering the product, so the results from the blood sample can be used to determine if or how much product to administer. For example, a user may sit on the toilet, the toilet takes a blood sample from the user, the sample is tested for a blood sugar test, the test results are used to determine how much insulin the user needs, the toilet inserts a hypodermic needle into the user to deliver a subcutaneous injection, the toilet delivers the determined amount of insulin, and the toilet removes the needle from the user. Additionally, the toilet may apply pressure to the injection site after the injection. In one preferred embodiment, the toilet cleans and/or sterilizes the hypodermic needle between uses. In another preferred embodiment, the hypodermic needle is disposed of after each use and new one is used for each subsequent use.

Enteral and transmucosal administration occurs when the body absorbs products through a mucus membrane, such as found in the rectum, urethra, other parts of the gastrointestinal tract, and vagina. These products may be inserted or injected in a variety of ways, such as a suppository, a cream, a solution, or an enema. They can be particularly useful when administering to a person with nausea or other digestive problems. As an example, a suppository can be inserted into rectum or vagina. Enemas or other products can be injected into the rectum. Additional products administered intravaginally include estrogens, progestogens, antibacterial to treat bacterial vaginosis, antifungals to treat yeast infections, and artificial insemination treatments.

In a preferred embodiment, the toilet includes a wand that extends from the toilet into a user's rectum, urethra, or vagina to administer the product. In one preferred embodiment, the want automatically extends to enter the user. In another preferred embodiment, the act of the user sitting on or standing in front of the toilet facilitates the wand entering the users. In still another preferred embodiment, the user controls the motion of the wand as a tool to help self-administer the product. In another preferred embodiment, a user sits down onto a suppository. In yet another preferred embodiment, the bidet squirts out the product such that the product forces itself into the rectum, urethra, or vagina.

Inhalation administered product are inhaled through the respiratory system and includes a wide variety of potential uses. A product may be in a gaseous state, may be a pressurized liquid that becomes gaseous when lowered to ambient pressures, may be a liquid that requires the addition of energy to become vaporized, or may even be a solid that off gasses or chemically reacts with the atmosphere to produce a gas. These products are meant to serve a variety of purposes, including improving the smell of the air, opening up the respiratory passages, hydrating the respiratory passages, calming the user, aromatherapy, and administering a product to be absorbed by the mucus membranes in the respiratory passages. Such products may include potpourri, perfumes, oils (notably essential oils), deodorizers, or other products that improve the smell in the air. They may include a humidifier or a product that get diffused into the air with water as the water is used by a humidifier. Medicaments that are administered through inhalation include bronchodilator or other asthma treatments, oxygen, steroids, mucolytics, surface hydrators, and antibiotics. In one preferred embodiment, the toilet contains a boiling or other vaporizing element to introduce the product into the air proximate to the toilet for inhalation by the user. Additionally, the product may be added to water before being vaporized. In one preferred embodiment, the toilet may include a respiratory mask to assist in administering the product to the user. Additionally, the toilet may include a consumable for cleaning the respiratory mask or pneumatic pathways.

A third general class of consumable is those useful in processing or analyzing excreta for use with a sensor that detects a property of the excreta, especially those properties related to a person's health and wellness. Possible consumables in this category include reagents which are useful for detecting infections, diseases, sicknesses, parasites, long term health conditions, and a long list of other items relevant to a person's health. Within each of these reagent categories listed are numerous sub-lists that include specifics like pregnancy, urinary tract infections, swine flu, tape worms, diabetes markers like glucose levels, stress hormones, etc. There are a variety of other desirable consumables outside of these classes too. Additionally, these classes are not necessarily mutually exclusive. One consumable may serve the function of more than one class and may therefore be used for multiple reasons.

In one preferred embodiment, the toilet takes a urine sample, adds a pregnancy test reagent, and analyzes the color of the resulting reaction to determine if the user is pregnant; as with other tests, this may not be a regularly occurring test, but one that is performed for a subset of users or as a one-time test requested for a rare user condition for which there is an increased suspicion that the user has the condition. Similarly, the toilet may collect a sample of excreta for a drug test.

In another preferred embodiment, a stabilizer may be added to stabilize an excreta sample against environmental factors or time before the toilet encapsulates it for transportation outside of the toilet or when there will be an extended period of time between when the sample is collected and when it is tested. Such stabilization can preserve the proteins from degrading. Additionally, lowering the temperature of the sample may help prevent bacteria in the sample from multiplying. In one preferred embodiment, a sample is deposited in a plastic container that has a UV inhibitor added to the plastic.

In one preferred embodiment, a sample of excreta is processed and/or analyzed where it comes to rest in the toilet. In an alternative embodiment, a sample of excreta is moved from its initial resting place in the toilet to a secondary location within the toilet for processing and/or analysis within the toilet. In one embodiment, the processing and/or analysis takes place in the same shroud in which the toilet bowl is contained. In another embodiment, the sample automatically travels out of the shroud enclosing the toilet bowl and to a processing and/or analysis location inside a separate apparatus. In another preferred embodiment, the toilet prepares a sample of excreta for transportation to another location such as a lab. This transportation includes possibly being carried by hand, being transported in a vehicle, going through a mail or parcel delivery service, an automated system such as artificial intelligence controlled robots, conveyers, drones, pneumatic systems, hydraulic systems. Preparation for this transportation may include encapsulating the sample in a protective structure, like a plastic container, a dissolving capsule, and/or a liquid. It may include stabilizing the sample against the degradation of relevant analytes. In some embodiments, the stabilization will include the use of chemicals. In other embodiments, the stabilization will include characteristics of the container, such as UV stabilization in plastic to prevent UV exposure from affecting the sample. In yet other embodiments, environmental controls may be necessary to preserve the sample during transport such as temperature, pressure, or humidity control. More preferably, the environmental controls preserving the sample automatically adjust based on monitoring environmental elements of the sample compared to a predetermined preference for what those elements should be. In one preferred environment the toilet prepares the sample for transport by including ice, a chilled container, or another cooling agent.

Each consumable product in the toilet may be unique in many ways, including the length of time it will be stored in the toilet, the amount used for use, an optimal temperature, an optimal pressure, and an optimal humidity. Each of these factors may contribute to when a new supply of the consumable product needs to be provided in order to maintain a usable amount of consumable product within the toilet. Therefore, there may be a test or criterion created relative to any of these factors singly or in combination with other factors. Additionally, the test or criterion may require determining a property or state of a consumable product or its surrounding environment. To speed things up, a predetermined preference or criterion can be input by a person or automatically generated by an algorithm.

Additionally, some properties of the consumable may determine how the consumable is used. For example, if the consumable product is being mixed with water to form a solution, the pH of the consumable may be relevant in determining the ratio of how much of the consumable to mix in with the water. Similarly, other properties of a consumable, such as its concentration may help determine how much to mix in with water or other consumables.

Depending on the use within the toilet, some consumables may be needed in larger quantities than others. One preferred embodiment may provide for a single size volume or cartridge for a consumable. Another embodiment may provide multiple size options of volume or cartridge for a consumable product.

Some consumables may expire after a certain amount of time has passed (i.e., lose their reactivity or effectiveness over time). Therefore, some embodiments of the toilet may monitor the length of time a consumable has been in the toilet. Additionally, it may be desirable to test a reagent to determine if a reagent or other consumable is still useable, so sensors and other testing mechanism may be included in the design.

Some consumables may expire due to a sensitivity to temperature, pressure, light, or humidity. Therefore, an embodiment of the toilet may include a controlled environment or temperature, pressure, light, and/or humidity control for the consumable while it is in the storage structure. This control could require general isolation and/or insulation from other parts of the toilet or environment the toilet is in. Control measures could include refrigeration, a heat source, a light barrier such as a shroud or cover, a humidifier, and/or a dehumidifier.

Sensors do not necessarily provide the specific data or information being sought. Rather, sensor data is often used in conjunction with other data and/or post-processing to arrive at the desired information. For example, an image sensor may be used to take a picture of a consumable product in a transparent or translucent container. The image it creates has no inherent value, but additional information can be used provide relevant data. In one example, an algorithm could analyze the image to determine the height of a liquid consumable. Additionally, the height could be used in combination with geometric information about the container holding the liquid to determine the volume of the consumable. Such information could be used to determine if there is sufficient consumable available for anticipated future use. In another example, an algorithm could analyze the image to determine the color of the consumable. The color may be linked to relevant information such as the identity of the consumable or the remaining life expectancy of the consumable. Thus, a sensor is used to detect a state of, i.e. one or more properties of, a consumable stored in the toilet.

Following are some examples of states or properties of a consumable that data from a sensor may be used to help determine:
  Detecting whether or not any consumable product and/or consumable container is loaded in the storage area;
  Determining whether a consumable is properly loaded into the storage structure;
  Identifying a consumable;
  Determining the quantity of consumable stored in the storage area;
  Measuring the temperature of a consumable;
  Detecting the color of a consumable;
  Measuring the pH of a consumable;
  Measuring the concentration of a consumable.

There are many reasons for detecting such properties of a consumable, including the generation of an alert based on a predetermined preference or criterion related to or incorporating a property of a consumable product. One reason may be verifying a desired consumable is in the storage area and ready for the toilet to use. Another use may be using the consumable identity to retrieve more information regarding the handling and use of the consumable (e.g., acceptable temperatures for a particular consumable). Still other uses include forecasting future consumable use, providing an alert that a consumable is running low, keeping track of how soon a consumable may expire or go bad, recommending additional consumable be ordered, and automatically ordering consumable.

The toilet could use sensor data to determine the state of a consumable (related to these and other reasons for wanting to detect a property of the consumable). Alternatively, the toilet could transmit sensor data about a consumable to the cloud or another processing location outside of the toilet to determine the state of a consumable relative to said reasons. Additionally, some data processing could be completed within the toilet before the data is transmitted, including using a digital signal processor to change the signal. In some embodiments, it may be desirable to receive information regarding the remotely determined state or some other information related to a consumable in the toilet, therefore the consumable management system of the toilet may connect with a receiver for receiving external electronic data.

There are many types of sensor that could be implemented to detect desired state information. The selection of which sensor or sensors to use will depend on a number of factors, including, the consumable or consumables to be used, space requirements, materials of construction, and what properties are relevant to detect. For example, the presence of a consumable product or container could be detected by sensors such as a switch that depresses when the consumable is loaded into the storage structure; a pressure or weight sensor that changes reading when a consumable is loaded into the storage structure; an image sensor that would show when a consumable is loaded into the storage structure; a spectrometer could detect the spectrometry of the consumable when it is loaded in the storage area; a proximity sensor that could detect the distance of a consumable or consumable container relative to the sensor; an RFID, barcode, or QR code reader that reads an RFID chip, barcode, or QR code with the consumable; a height of a float could change with the height of a consumable, especially a liquid consumable. Additionally, some of these sensors could also be used to identify the consumable, determine the quantity or supply of consumable available in the storage area, temperature, or other properties of the consumable.

Once a state of a consumable property has been detected by a sensor and represented as an electric signal, many things can happen with that data, including it can be transmitted to a controller, processed so it's more usable, converted to other units (such as converting a pressure into a weight or converting a fluid height into a volume), stored in long-term or short-term memory, compared with other data (including preferences selected by a person or algorithm), removed from memory, and/or transmitted to a receiver.

In one preferred embodiment, a controller or processor generates an alert or signal which is used to provide information which may result in controlling a property or function of the toilet related to the consumable. This may be done as the processor receives the state data resulting from the sensor detecting a state of the consumable product. Following which, the controller can process and/or compare the data to historical and/or external data. Based on this processing or comparison, the controller alert can restrict or enable features of the toilet. Such features include, reporting on the state of the consumable, ordering or requisitioning a new supply of the consumable, providing a maintenance alert, using the consumable, and removing waste from the toilet. In one preferred embodiment, the processor is in the toilet. Alternatively, the controller or processor is external to the toilet and is communicably connected to the toilet. This could be within the cloud, a phone, or other device.

In one preferred embodiment, the toilet has access to read a database of known consumables. In another embodiment, the toilet could transmit data about a consumable to an external location for comparison to an external database of known consumables. In either case, the toilet may be set up to receive information from a database of known consumables. Again, in either case, data regarding a consumable could be compared to a database of known consumables and/or could prompt the database to provide additional information about a consumable regarding the consumable's preservation, preferred, or necessary storage requirements, use, disposal, or other relevant information. This information can be used to automatically determine an action to be taken relative to or regarding the consumable, such as maintaining a specific temperature or temperature range, maintaining a desired humidity, maintaining a desired pressure, providing a maintenance alert, ordering additional consumable, and activating or deactivating a feature of the toilet that is contingent upon the presence or absence of the consumable.

In some preferred embodiments, the toilet monitors a consumable specifically for the purpose of automatically assisting in making sure there is always enough of a consumable in the toilet ready for use. There are many ways to provide this assistance. In general, the amount or quantity of a consumable product is compared to a predetermined threshold or level and an alert is generated from a processor if the supply of consumable product is un-preferred. In one preferred embodiment, the toilet monitors the amount of a consumable, compares that amount to a user specified threshold minimum, and provides an alert if the consumable quantity drops below the minimum. In an alternative preferred embodiment, the toilet may automatically purchase additional consumable if the consumable quantity drops below the minimum. In an alternative preferred embodiment, the toilet calculates a preferred minimum quantity of consumable based on past and forecasted usage data rather than receiving a user specified minimum (the time required to order, ship, and receive new consumable may also be taken into account). In another preferred embodiment, the toilet calculates a preferred minimum using at least one piece of preference data from an external source, such as a user preference or a database with information regarding the consumable. Alternatively, the toilet may monitor a consumable that has a positive growth rate to ensure that there is not too much consumable, such as a supply of bacteria that multiplies faster than it is administered or used or liquid that off-gasses in a pressurizable container wherein too much could result in an undesirable or preventable maintenance issue.

There are many systems that can be used to obtain a consumable product. In one preferred embodiment, a consumable product is purchased using a "just in time" approach so the consumable spends a minimal amount of time after it arrives before being stocked or put inside the toilet for active use. In this case, the state of the consumable may indicate it is near to expiring or running out and may result in the automatic reordering of the consumable. In another preferred embodiment, a product is purchased well in advance of being put inside the toilet for active use and may be stored in or out of the toilet as inventory. In cases where product is inventoried before being put into active use, a method of inventory management may be used to monitor what has been purchased but is unused and therefore still available for use to restock a consumable supply. In such a system, the inventory count generally has to be updated when a product is taken out of inventory and put into active use. The term "requisition" can be used to represent a request to order a new supply of consumable, a request to remove consumable from inventory, or a variety of similar steps that result in increasing the supply of a consumable product that is available for use by the toilet. One example, that is a hybrid of "just in time" and inventory systems, is the purchase of a three pack of the same consumable product in which one is put into the toilet for active use and the other two are stored on a shelf, the items on the shelf are recorded as inventory, and they have to be removed from inventory when put into the toilet for active use.

In some preferred embodiments, the toilet provides a user interface to represent information regarding the state of the consumable. In one preferred embodiment, the toilet may be configured to provide a visual indication of whether the quantity of consumable available is outside a desired threshold, such as a minimum or maximum quantity. Alternatively, the user interface could provide other information relative to the consumable, such as amount remaining, percent remaining, number of uses worth of consumable remaining, expected refill date, temperature, pressure, moisture content or humidity, age, or a variety of other relevant information that would assist people in maintaining the toilet for use. The units for the visual indication of the state of the consumable will depend on those of the initial sensor data, any processes the data has gone through, and preferences for how the data is displayed. Alternatively, an external device or program may be configured to provide a visual indication of the same, including a display showing an optical image of the consumable, or a computer, web portal, or mobile device with an app that displays information regarding the consumable. The toilet may also include a user interface or control to control functions such as the toilet's self-cleaning functions and/or a bidet system. In any of these cases, a consumable in the toilet may be for cleaning the surfaces a user may contact on a user interface.

Data processing described as being performed by the toilet could also be performed outside the toilet. Therefore, in some embodiments the toilet may be equipped to transmit product or consumable related data to an external location. Additionally, it may be desirable for the toilet to receive information relevant to the consumable, therefore in some embodiments the toilet may be equipped with to receive data from an external location. Data transmission and reception can both be accomplished through wired, wireless, optical, or other non-wired transmission media and the relevant hardware to facilitate use of the media, including ethernet, wi-fi, z-wave, fiber optic, and data encoded sound waves.

The disclosure could apply to the storage, monitoring, and disposal of excreta between when the excreta is deposited into the toilet and when the excreta is removed from the toilet. This could be particularly important during the any pre-analysis preparation stages as specific conditions may be required or desired for an analysis to take place. The disclosure could also be applied to the storage, monitoring, and disposal of used consumables, unprocessed or post-processed excreta, or combinations thereof.

All patents, published patent applications, and other publications referred to herein are incorporated herein by reference. The invention has been described with reference to various specific and preferred embodiments and techniques. Nevertheless, it is understood that many variations and modifications may be made while remaining within the spirit and scope of the invention.

What is claimed is:

1. An analytical toilet comprising:
   a bowl adapted to receive excreta;
   a mechanism that uses a consumable for analyzing a sample of excreta;
   a storage structure for storing the consumable;
   a sensor that detects at least one property of the consumable stored by the storage structure, wherein the property can be used to determine at least one of an identity of the consumable, a quantity or supply of the consumable, and a property related to a suitability of the consumable; and
   a processor that generates an alert when the property of the consumable is outside a predetermined parameter.

2. The analytical toilet of claim 1, wherein the predetermined parameter is an identity of a desired consumable, and wherein the property of the consumable is indicative of the identity of the consumable.

3. The analytical toilet of claim 1, wherein the predetermined parameter is a desired quantity or supply of the consumable in the storage structure, and wherein the property of the consumable is indicative of the quantity or supply of the consumable in the storage structure.

4. The analytical toilet of claim 1, wherein the predetermined parameter is related to an environmental condition of the consumable, and wherein the property of the consumable is indicative of the environmental condition of the consumable.

5. The analytical toilet of claim 4, wherein the alert is used to adjust an environmental control controlling the environmental condition of the consumable.

6. The analytical toilet of claim 5, wherein the adjustment to the environmental control is automatic.

7. The analytical toilet of claim 1, wherein the alert controls whether a specific analysis related process is performed by the toilet.

8. The analytical toilet of claim 1, wherein the consumable comprises a portion that is used by the mechanism and a portion that serves as a container which cooperates with the storage structure to store the consumable.

9. The analytical toilet of claim 1, wherein the consumable comprises a reagent.

10. The analytical toilet of claim 1, wherein the consumable comprises one or more test strip.

11. The analytical toilet of claim 1, wherein the consumable is used to prepare or stabilize excreta for analysis.

12. The analytical toilet of claim 1, wherein the preparation of the excreta for analysis comprises encapsulating a sample of excreta for transport.

13. The analytical toilet of claim 1, wherein the consumable is added to the samples of excreta as part of the analysis.

14. The analytical toilet of claim 1, wherein the consumable is used in conjunction with preparing the sample for disposal.

15. The analytical toilet of claim 1, wherein the consumable is used to prepare excreta for disposal or removal from the toilet following analysis.

16. The analytical toilet of claim 1, wherein the analysis is related to the health or wellness of a user of the toilet.

17. The analytical toilet of claim 1, wherein the toilet cleans a portion of the toilet to improve integrity of analysis results.

18. The analytical toilet of claim 1, further comprising an additional storage structure for an additional consumable used in conjunction with cleaning the toilet.

19. The analytical toilet of claim 1, further comprising a manifold to direct the flow of the consumable or an excreta sample.

20. A method of managing a consumable in an analytical toilet comprising:
   providing an analytical toilet comprising:
      a bowl adapted to receive excreta;
      a mechanism that uses a consumable for analyzing a sample of excreta;
      a storage structure for storing the consumable;
      a sensor that detects at least one property of the consumable stored by the storage structure, wherein the property can be used to determine at least one of an identity of the consumable, a quantity or supply of the consumable, and a property related to a suitability of the consumable; and
      a processor that generates an alert based on a criterion of whether the detected property of the consumable is outside a predetermined parameter;
   using the sensor to detect the property of the consumable;
   using the processor to compare the detected property against the predetermined parameter; and
   using the processor to generate an alert when the property is outside the predetermined parameter.

* * * * *